United States Patent [19]

Firestone

[11] Patent Number: 4,564,635

[45] Date of Patent: Jan. 14, 1986

[54] ALLYLSULFOXIDE ENZYME INHIBITORS

[75] Inventor: Raymond A. Firestone, Fanwood, N.J.

[73] Assignee: Merck & Co., Inc., Rahway, N.J.

[21] Appl. No.: 663,925

[22] Filed: Oct. 23, 1984

Related U.S. Application Data

[60] Division of Ser. No. 498,344, May 26, 1983, Pat. No. 4,491,590, which is a division of Ser. No. 349,809, Feb. 18, 1982, Pat. No. 4,400,395, which is a division of Ser. No. 147,656, May 7, 1980, Pat. No. 4,332,813, which is a continuation-in-part of Ser. No. 66,603, Aug. 15, 1979, abandoned.

[51] Int. Cl.[4] .................. A61K 31/195; C07C 101/10
[52] U.S. Cl. ..................................... 514/562; 562/430
[58] Field of Search .................. 562/430; 424/319; 514/562

[56]  References Cited

PUBLICATIONS

March, J., *Advanced Organic Chemistry*, McGraw Hill, New York, 1968, p. 887.

*Primary Examiner*—Richard A. Schwartz
*Attorney, Agent, or Firm*—Daniel T. Szurs; William H. Nicholson; Mario A. Monaco

[57]  ABSTRACT

Organic sulfoxides having a latent allyl group bound to the sulfur are enzyme inhibitors of the suicide or $K_{cat}$ type.

6 Claims, No Drawings

ALLYLSULFOXIDE ENZYME INHIBITORS

This is a division of application Ser. No. 498,344, filed May 26, 1983, now U.S. Pat. No. 4,491,590, which in turn is a division of application Ser. No. 349,809, filed Feb. 18, 1982, now U.S. Pat. No. 4,400,395, which in turn is a division of application Ser. No. 147,656, filed May 7, 1980, now U.S. Pat. No. 4,332,813, which in turn, is a continuation-in-part of application Ser. No. 066,603, filed Aug. 15, 1979, now abandoned.

BACKGROUND OF THE INVENTION

This invention is concerned with a novel class of enzyme inhibitors of the suicide or $K_{cat}$ type in which the latent reactive group is an allylsulfoxide which is in reversible equilibrium with an allyl sulfenate:

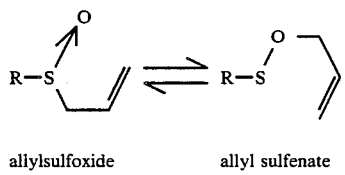

allylsulfoxide     allyl sulfenate     (A)

Suicide enzyme inhibitors are substances bearing a latent reactive group that is unmasked by the target enzyme itself, and which after being unmasked, immediately reacts with the enzyme in an irreversible manner, inactivating it. Enzyme inhibitors of the suicide type are known in the art but until now almost invariably have employed a Michael acceptor as the reactive species and these are described by Walsh in *Horizons Biochem. Biophys.*, 3, 36–81 (1977).

The allylsulfoxide-allyl sulfenate equilibrium of reaction scheme (A) is also known in the art and has been studied as an interesting chemical reaction by Mislow et al., *J. Amer. Chem. Soc.*, 90, 4869 (1968); 92, 2100 (1970) and Evans et al., *J. Amer. Chem. Soc.*, 94, 3672 (1972). Generally, allylsulfoxides are unreactive, but allyl sulfenates are highly reactive electrophiles, and would be expected to capture almost any nucleophile (Nu) in an enzyme that happens to be near it at the moment it is formed:

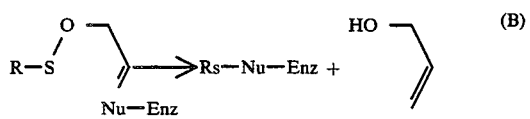

(B)

Usually the nucleophile is one from the protein portion (prosthetic group) of the enzyme, such as a sulfhydryl, amino, hydroxy, imidazolyl or the like. Once the nucleophile is sulfenylated, the enzyme is altered from its native, active form and can no longer function in its intended role as a biochemical catalyst.

The allylsulfoxide-allyl sulfenate rearrangement is facilitated by the nature of the R group attached to the sulfur: the stronger the electron withdrawing nature of R the better, for example, p-nitrophenyl. Steric acceleration of the rearrangement is also provided by bulky o-substituent such as o-alkyl and o,o'-dialkyl when R is substituted-phenyl. Bulky groups such as alkyl and chloro substituted on the carbon chain adjacent to the sulfur atom also provide steric acceleration.

In the present invention, the latency of the allylsulfoxide group is generally secured as a β- or γ-halosulfoxide wherein the halo is also β- to the carboxyl group of an α-amino acid which the target enzyme recognizes as a potential substrate. On attack by the enzyme the amino acid is decarboxylated, and splits out halide ion to produce the allylsulfoxide.

In the present invention, the allyl sulfoxide type of inhibitor advantageously also is combined with other types of inhibitor in the same molecule such as the fluoromethyl dopa decarboxylase, histidine decarboxylase, or the tryptophane decarboxylase inhibitors. In these cases, the bifunctionality creates inhibitors with great efficiency, doubling the sites for nucleophilic attack, as shown below:

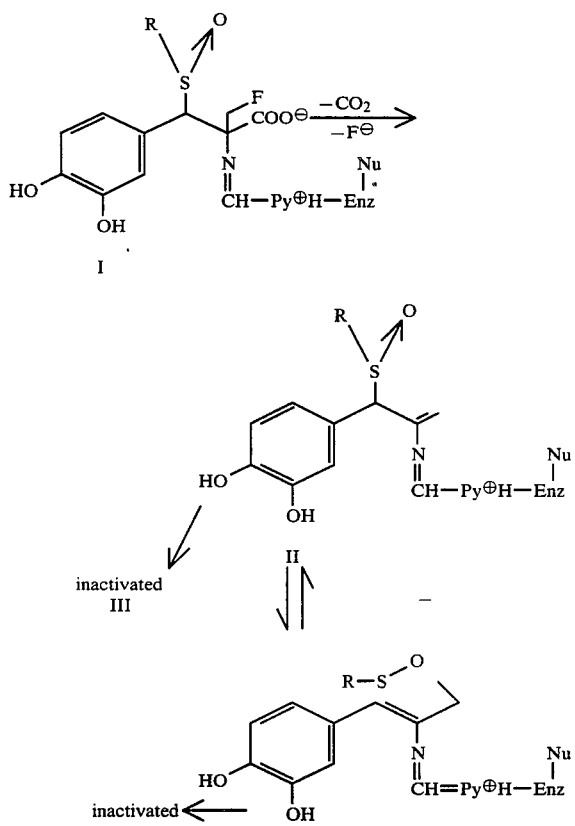

The mechanism of inhibition, I→II→III is that of Kollonitsch et al., *Nature*, 274, 906 (1978).

It is, therefore, an object of this invention to provide a group of novel organic sulfoxides wherein one of the substituents on the sulfur carries such other functional group or groups as to be a latent allyl group which becomes unmasked upon reaction with a target enzyme and which function as enzyme inhibitors of the suicide type.

It is another object of this invention to provide a useful tool of biochemical research in the form of selective, very active enzyme inhibitors.

It is a further object of this invention to provide means for inhibiting enzymes, both in vitro and in vivo with the novel organic sulfoxides of this invention.

It is a still further object to provide a method of treating disease states, the progress of which is dependent on the activity of enzymes, which comprises the administration of an effective amount of an enzyme inhibitor of this invention.

It is also an object of this invention to provide pharmaceutical formulations comprising one or more of the novel enzyme inhibitors of this invention.

DETAILED DESCRIPTION OF THE INVENTION

This invention comprises, as one embodiment, a new class of $K_{cat}$ or suicide enzyme inhibitors, which are organic sulfoxides of formula:

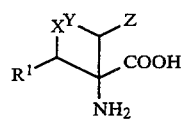

or a pharmaceutically acceptable salt thereof, wherein X is hydrogen, fluoro, chloro, bromo, iodo, $C_{2-4}$ alkanoyloxy, toluenesulfonyloxy, benzenesulfonyloxy, $C_{1-3}$ alkanesulfonyloxy, p-nitrobenzoyloxy, or the like, or

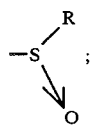

Y is hydrogen or

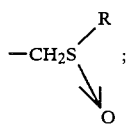

and Z is fluoro, chloro, bromo, iodo, $C_{2-4}$ alkanoyloxy, toluenesulfonyloxy, benzenesulfonyloxy, $C_{1-3}$ alkanesulfonyloxy, p-nitrobenzoyloxy, or the like, or

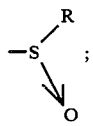

or Y and Z taken together form =CH$_2$; with the proviso that one and only one of X, Y and Z is a sulfoxide group, and one and only one of X and Z is fluoro, chloro, bromo, iodo, $C_{2-4}$ alkanoyloxy, toluenesulfonyloxy, benzenesulfonyloxy, $C_{1-3}$ alkanesulfonyloxy, p-nitrobenzoyloxy, or the like; wherein R is
(a) phenyl, either unsubstituted or substituted with such as:
  (1) nitro,
  (2) cyano,
  (3) $C_{1-3}$ alkylsulfonyl,
  (4) $C_{1-3}$ alkoxycarbonyl,
  (5) o-$C_{1-3}$ alkyl,
  (6) o,o'-di($C_{1-3}$alkyl), or
  (7) di(trifluoromethyl);

(b) trihalomethyl such as
  (1) trifluoromethyl, or
  (2) trichloromethyl;
(c) 5-6 membered heteroaryl such as
  (1) thiazolyl,
  (2) imidazolyl,
  (3) pyridinyl,
  (4) pyrazinyl,
  (5) oxazolyl
  (6) pyrimidinyl, or
  (7) thienyl; and
$R^1$ is
  (a) imidazol-4-yl,
  (b) 3,4-dihydroxyphenyl,
  (c) aminoethyl,
  (d) 5-hydroxyindol-3-yl,
  (e) 4-hydroxyphenyl, or
  (f) hydrogen.

Many disease states of mammals, including humans, are known to depend for their progress on the activity or hyperactivity of particular enzymes and treatment of many of these diseases have been devised around inhibitors of these enzymes. Accordingly, the novel enzyme inhibitors of this invention have utility in the study of certain disease states and in their treatment.

Generally the novel enzyme inhibitors of this invention produce the desired effect when administered at from 0.1 to about 500 mg/kg body weight, preferably at from 1 to about 50 mg/kg of body weight. The preferred form of delivery of the instant compounds to domestic animals is by solution in drinking water or by inclusion in preformulated feedstuffs. For human and animal administration, any of the usual pharmaceutical oral forms may be employed such as tablets elixirs, aqueous suspensions or the like comprising from about 0.1 to about 500 mg of the compounds of this invention. Sterile solutions (representatively given for human treatment) for injection comprising from about 0.1 to about 500 mg of the compounds of this invention given two or four times daily are also suitable means of delivery.

Representative specific members of the new class of suicide enzyme inhibitors are shown in Table I along with the enzyme to be inhibited and the pharmacological or medical effect to be elicited. In each case, R represents o- or p-nitrophenyl, o- or p-cyanophenyl, o or p-methoxycarbonylphenyl, o- or p-methylsulfonylphenyl, o,p-di(trifluoromethyl)phenyl, trifluoromethyl, trichloromethyl, 2-pyrimidinyl, 2-pyridyl, 2-imidazolyl, 2-thienyl, 2-thiazolyl, 2-oxazolyl, o-methylphenyl, o-ethylphenyl, o-propylphenyl, o,o-di(methyl)phenyl, o,o-di(ethyl)phenyl, or o,o-di(propyl)phenyl.

TABLE I

| INHIBITOR | ENZYME INHIBITED | USE, PHARMACOLOGICAL OR MEDICAL EFFECT |
|---|---|---|
| (structure: imidazole-CH(S(O)R)-CF(COOH)(NH2)) | histidine decarboxylase | antihistamine |
| (structure: imidazole-CH2-CH(F)-... with CH2-S(O)R, COOH, NH2) | | |
| (structure: imidazole-CH(Cl)-C(CH2S(O)R)(NH2)(COOH)) | histidine decarboxylase | antihistamine |
| (structure: imidazole-CH(S(O)R)-C(=CH-)COOH, NH2) | | |
| (structure: 3,4-dihydroxyphenyl-CH(S(O)R)-CF(COOH)(NH2)) | dopa decarboxylase | antihypertensive antiparkinson when administered with L-dopa |
| (structure: 3,4-dihydroxyphenyl-CH2-CH(F)-C(CH2S(O)R)(COOH)(NH2)) | | |

TABLE I-continued

| INHIBITOR | ENZYME INHIBITED | USE, PHARMACOLOGICAL OR MEDICAL EFFECT |
|---|---|---|
| [structure: 3,4-dihydroxyphenyl with CHCl-CH(NH2)(COOH)-CH2-S(O)R] | dopa decarboxylase | antihypertensive antiparkinson when administered with L-dopa |
| [structure: 3,4-dihydroxyphenyl with CH(SR(O))-C(=CH2)(NH2)(COOH)-type vinyl] | | |
| [structure: H2N-CH2CH2CH2-CH(SR(O))-CF(COOH)(NH2)] | ornithine decarboxylase | anti-psoriasis anti-arthritis anti-cancer |
| [structure: H2N-CH2CH2CH2-CH(SR(O))-CH2-CF(COOH)(NH2) type, wait: H2N...CH(SR(O))CH2-C(F)(COOH)(NH2)] | | |
| [structure: H2N-CH2CH2CH2-CHCl-CH(SR(O))-CH(COOH)(NH2)] | ornithine decarboxylase | anti-psoriasis anti-arthritis anti-cancer |
| [structure: H2N-CH2CH2CH2-C(SR(O))=C(COOH)(NH2) vinyl] | | |
| [structure: H2N-CH2-S(O)-CH(H)-CF(COOH)(NH2)] | | |

TABLE I-continued
| INHIBITOR | ENZYME INHIBITED | USE, PHARMACOLOGICAL OR MEDICAL EFFECT |
|---|---|---|
| 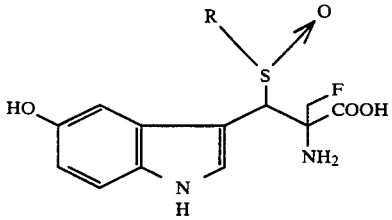 | tryptophan decarboxylase | antiserotonin |
| 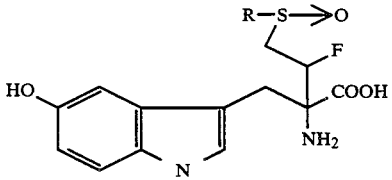 | | |
| 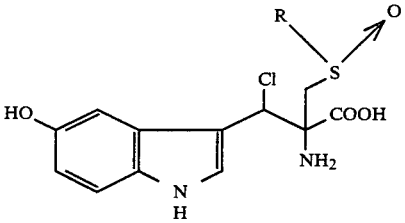 | tryptophan decarboxylase | antiserotonin |
| 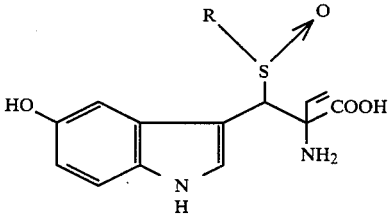 | | |
| 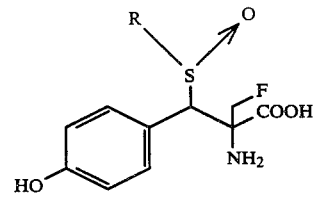 | tyrosine hydroxylase | antihypertensive |
| 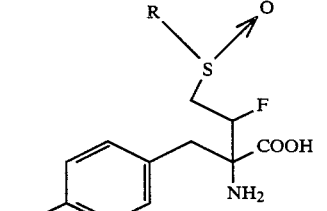 | | |
| 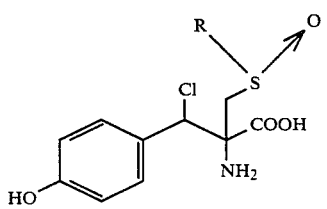 | tyrosine hydroxylase | antihypertensive |

TABLE I-continued

| INHIBITOR | ENZYME INHIBITED | USE, PHARMACOLOGICAL OR MEDICAL EFFECT |
|---|---|---|

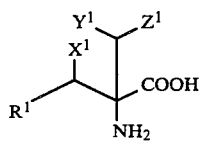

The novel process for preparing the novel compounds of this invention comprises oxidation of an aromatic thio compound of structure:

wherein $X^1$ is hydrogen, fluoro, chloro, bromo, iodo, $C_{2-4}$ alkanoyloxy, toluenesulfonyloxy, benzenesulfonyloxy, $C_{1-3}$ alkanesulfonyloxy, p-nitrobenzoyloxy, or the like, or

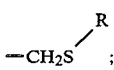

$Y^1$ is hydrogen or

and $Z^1$ is fluoro, chloro, bromo, iodo, $C_{2-4}$ alkanoyloxy, toluenesulfonyloxy, benzenesulfonyloxy, $C_{1-3}$ alkanesulfonyloxy, p-nitrogenzoyloxy, or the like, or

—S$^R$ ;

or Y and Z taken together form =CH$_2$; with the proviso that one and only one of X, Y and Z is a thio group, and one and only one of X and Z is fluoro, chloro, bromo, iodo, $C_{2-4}$ alkanoyloxy, toluenesulfonyloxy, benzenesulfonyloxy, $C_{1-3}$ alkanesulfonyloxy, p-nitrobenzoyloxy, or the like; and R, and $R^1$ are as previously defined with the exception that any of the substituents which are sensitive to the conditions of oxidation of sulfide to sulfoxide carry protective groups.

The oxidizing agent is such as 1-chlorobenzotriazole, $H_2O_2/V_2O_5$, $SO_2Cl_2/H_2O$/silica gel, $Cl_2$, $Br_2$, $NaIO_4$, acetyl nitrate, $Tl(NO_3)_3$, or a peracid such as m-chlorperbenzoic acid, preferably the latter. The oxidation with a peracid is conducted at temperatures from $-70°$ C. to about $30°$ C., preferably at about $0°-25°$ C., in an organic solvent such as an aromatic solvent, for example benzene, toluene or the like; or a chlorinated hydrocarbon such as tetrachloroethylene, chloroform, methylene chloride or the like, for times of a few minutes to about 4 hours.

After the oxidation is substantially complete, any protective groups present are removed by standard procedures such as treatment with a strong organic acid such as trifluoroacetic acid to remove t-butyloxycarbonyl groups from amines and to cause deesterification; strong mineral acids to remove trityl groups from amines; and strong bases such as sodium hydroxide or potassium hydroxide to saponify esters.

EXAMPLE 1

2-Fluoromethyl-3-(p-nitrophenylsulfinyl)histidine hydrochloride

Step A: Preparation of N$_α$-phthaloyl-2-fluoromethylhistidine methyl ester (1·I)

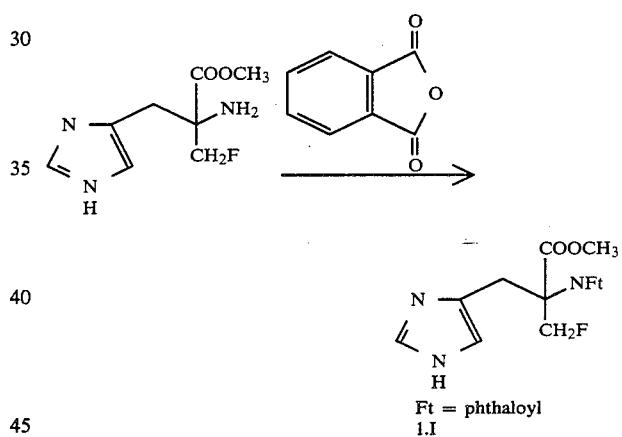

2-Fluoromethyl histidine methyl ester, 2.01 g (10 mmoles) and 1.48 g of phthalic anhydride (10 mmoles) are ground together in a mortar and then heated together 2 hours at 150° C. to form compound 1·I.

Step B: Preparation of N$_{Im}$-trityl-N$_α$-phthaloyl-2-fluoromethylhistidine methyl ester (1·II)

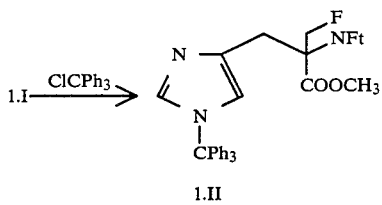

Compound 1·I, 331 mg (1 mmole), is treated with 278.5 mg (1 mmole) of trityl chloride in 25 ml of DMF containing 139 μl of triethylamine (1 mmole) overnight. The DMF is pumped off in vacuo and the residue is taken up in benzene, is washed with dilute aqueous sodium bicarbonate three times, then brine, then dried

Step H: Preparation of 2-fluoromethyl-3-(p-nitrophenylsulfinyl)histidine hydrochloride (1·VIII)

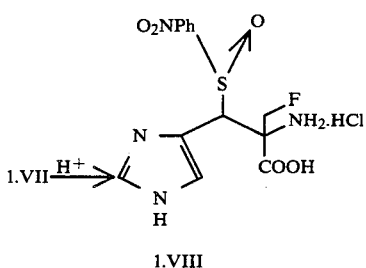

1·VIII

Compound 1·VIII, 598 mg (620 mg as the Na salt) of (1 mmole), is refluxed 3 hours with 25 ml of 6N HCl in MeOH containing 5% by volume of water to remove the trityl group. The reaction mixture is evaporated to dryness in vacuo, triturated with ether, taken up in ethanol, filtered and evaporated to afford compound 1·VIII.

EXAMPLE 2
2-([1-Fluoro-2-p-nitrophenylsulfinyl]ethyl)histidine hydrochloride

Step A: Preparation of N-benzylidene histidine methyl ester (2·I)

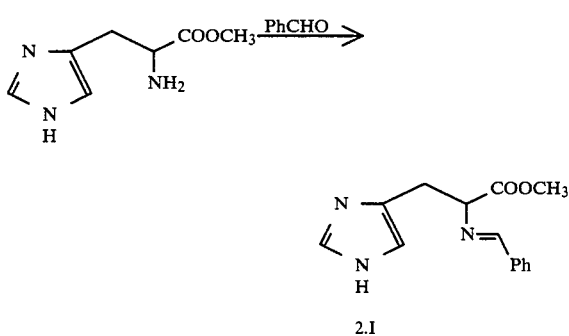

2·I

Histidine methyl ester, 185 mg (1 mmole), is treated with 1.06 g (1 mmole) of benzaldehyde in 25 ml of CHCl₃ for 3 hours. MgSO₄, 0.2 g, is added for the last hour. The mixture is filtered and the solvent is evaporated, to leaving compound 2·I as a residue.

Step B: Preparation of $N_{Im}$-trityl-$N_\alpha$-benzylidene histidine methyl ester (2·II)

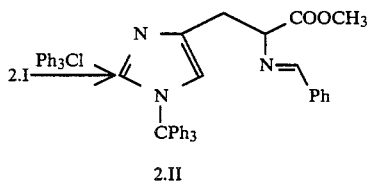

2·II

Compound 2·I, 273 mg (1 mmole) is treated with 278.5 mg (1 mmole) of trityl chloride in 25 ml of DMF containing 139 μl of triethylamine (1 mmole) overnight. The DMF is pumped off in vacuo and the residue, taken up in benzene, is washed with dilute aqueous sodium bicarbonate three times, then brine, then dried with K₂CO₃. Filtration and evaporation of the solvent afford compound 2·II.

Step C: Preparation of $N_{Im}$-trityl-$N_\alpha$-benzylidene-2-(1-hydroxyethyl)histidine methyl ester (2·III)

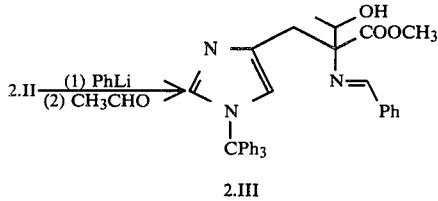

2·III

Compound 2·II, 516 mg (1 mmole), in 20 ml THF under N₂ at −78° C., is treated with 1 mmole of phenyllithium for 1 minute, forming the anion. Acetaldehyde, 44 mg (1 mmole) in 1 ml of THF is then added, and the mixture is allowed to warm slowly to room temperature. After evaporation of the solvent and replacement with CHCl₃, the sample is washed with water, then brine, then dried with K₂CO₃ and filtered. The filtrate is used directly in the next step.

Step D: Preparation of $N_{Im}$-trityl-$N_\alpha$-benzylidene-2-(1-tosyloxyethyl)histidine methyl ester (2·IV)

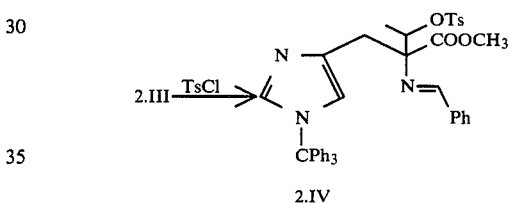

2·IV

To the solution of compound 2·III from Step C is added 0.5 ml of pyridine and then 190.5 mg (1 mmole) of tosyl chloride. After 30 minutes at 25° C. the solution is washed three times with water, once with brine, and dried with K₂CO₃ and filtered. The filtrate is used directly in the next step.

Step E: Preparation of $N_{Im}$-trityl-$N_\alpha$-benzylidene-2-vinyl histidine methyl ester (2·V)

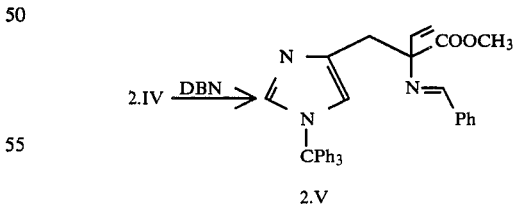

2·V

The solution of compound 2·IV from Step D is evaporated, taken up in benzene and refluxed 3 hours with 124 mg (1 mmole) of diazabicyclononane (DBN). The solution is washed twice with water, once with brine, and dried with K₂CO₃. Filtration and evaporation afford compound 2·V.

Step F: Preparation of $N_{Im}$-trityl-2-vinylhistidinemethyl ester (2·VI)

over K₂CO₃. Filtration and evaporation of the solvent affords 1·II.

Step C: Preparation of N$_{Im}$-trityl-N$_α$-phthaloyl-2-fluoromethyl-2'-trimethylsilyl histidine methyl ester (1·III)

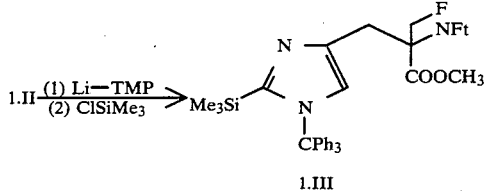

1·III

Lithium 2,2,6,6-tetramethyl piperidide (LiTMP) (1 mmole) is prepared as follows: To 141 mg of TMP (1 mmole) in 10 ml of THF at −18° C. under N₂ is added 1 mmole of n-butyllithium. The solution is then aged 15 minutes at 0° C. To it is then added a solution of compound 1·II, 573 mg (1 mmole), in 10 ml of THF at −78° under N₂. The reaction mixture is aged 30 minutes at −78° C. and 10 minutes at 0° C. and then treated at −78° C. with a solution of 127 μl (1 mmole) of trimethyl silyl chloride in 2 ml of THF. The reaction is allowed to warm to room temperature over 30 minutes. The solution of 1·III thus obtained is used directly in the next step.

Step D: Preparation of N$_{Im}$-trityl-N$_α$-phthaloyl-2-fluoromethyl-3-(p-nitrophenylthio)-2'-trimethylsilylhistidine methyl ester (1·IV)

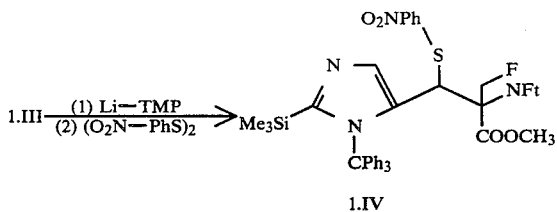

1·IV

The solution of 1·III from Step C is treated with a second mmole of LiTMP as before. Then at −78° C. this is added to a suspension of 308 mg (1 mmole) of very finely ground bis-(p-nitrophenyl)disulfide in 25 ml of THF. With vigorous stirring, this reaction mixture is allowed to warm to room temperature over 20 minutes, and then refluxed for 30 minutes. The solvent is evaporated, and the residue is taken up in 30 ml of benzene, washed twice with 1N aqueous NaOH, then with dilute aqueous HCl, then with brine. After drying over MgSO₄, filtration and evaporation of the solvent, there is obtained compound 1·IV.

Step E: Preparation of N$_{Im}$-trityl-N$_α$-phthaloyl-2-fluoromethyl-3-(p-nitrophenylsulfinyl)-2'-trimethylsilylhistidine methyl ester (1·V)

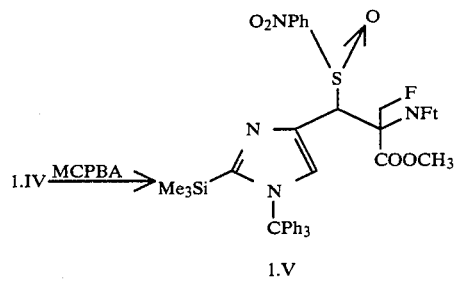

1·V

To 798 mg of compound 1·IV (1 mmole) in 25 ml of CH₂Cl₂ is added dropwise over 1 hour a solution of 203 mg of 85% pure MCPBA (net 172.6 mg; 1 mmole) in 20 ml of CH₂Cl₂. The solution is aged 30 minutes at 25° C. and washed successively with aqueous NaHCO₃ and brine. Evaporation gives compound 1·V.

Step F: Preparation of N$_{Im}$-trityl-N$_α$-phthaloyl-2-fluoromethyl-3-(p-nitrophenylsulfinyl)-histidine (1·VI)

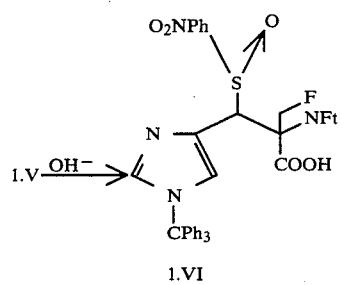

1·VI

Compound 1·V, 814 mg (1 mmole), is heated 2 hours at 50° C. with 30 ml of 2N NaOH in 3:2 (v/v) H₂O—MeOH with stirring. Water, 50 ml, is then added, the pH is adjusted to 2.0 with aqueous HCl, and the product is extracted with 3×30 ml of CH₂Cl₂. The organic extracts are combined, washed with brine, dried with MgSO₄, filtered and evaporated to provide compound 1·VI.

Step G: Preparation of N$_{Im}$-trityl-2-fluoromethyl-3-(p-nitrophenylsulfinyl)histidine (1·VII)

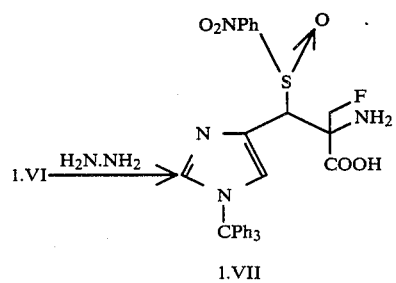

1·VII

The phthaloyl group is removed by refluxing 728 mg of compound 1·VI (1 mmole) with 96 mg of hydrazine hydrate (3 mmoles) in 20 ml of EtOH for 2 hours. Aqueous NaOH, 1 mmole, is added, and the reaction mixture is pumped to dryness at 0.1 Torr. Toluene is added and pumped off at 0.1 Torr to remove traces of hydrazine. The product is separated from phthaloyl hydrazide by taking it up in aqueous NaHCO₃ and washing with CH₂Cl₂. Evaporation of the water affords compound 1·VII as the sodium salt.

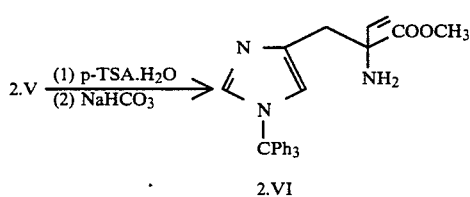

Compound 2·V from Step E is taken up in anhydrous ether and added dropwise over 10 minutes to a solution of 190 mg of p-TSA·H₂O (1 mmole) in 20 ml of ether. The toslyate salt of 2·VI precipitates out. It is collected by decantation, and stirred with ether and aqueous sodium bicarbonate. The ether phase is separated from the aqueous layer, washed with brine, dried with $K_2CO_3$, filtered and evaporated to yield compound 2·VI.

Step G: Preparation of $N_{IM}$-trityl-2-vinyl-$N_\alpha$-BOC-histidine methyl ester (2·VII)

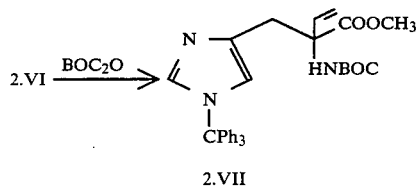

Compound 2·VI, 454 mg (1 mmole), is stirred with 218 mg of (BOC)₂O in 30 ml of CH₂Cl₂ for 3 hours at 25° C. and then washed successively with water and brine, and dried with $K_2CO_3$. Filtration and evaporation provides compound 2·VII.

Step H: Preparation of $N_{Im}$-trityl-2-([1-chloro-2-p-nitrophenylthio]ethyl)-$N_\alpha$-BOC-histidine methyl ester (2·VIII)

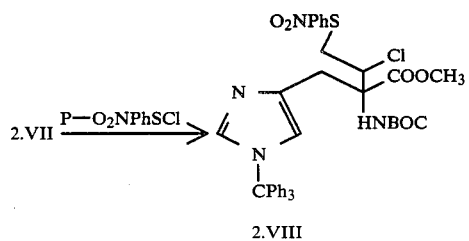

To 554 mg (1 mmole) of compound 2·VIII in 25 ml of CH₂Cl₂ at −18° C. is added dropwise over 30 minutes a solution of 190 mg (1 mmole) of p-nitrophenylsulfenyl chloride in 10 ml of CH₂Cl₂. The reaction is aged 30 minutes at room temperature and evaporated to afford compound 2·VIII.

Step I: Preparation of $N_{Im}$-trityl-2-([1-fluoro-2-p-nitrophenylthio]ethyl)-$N_\alpha$-BOC-histidine methyl ester (2·IX)

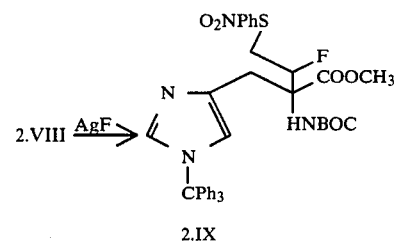

Compound 2·VIII, 744 mg (1 mmole), is stirred overnight in 30 ml of dry acetonitrile with 127 mg (1 mmole) of silver fluoride. The precipitated silver chloride is separated by centrifugation and the solvent is evaporated to afford compound 2·IX.

Step J: Preparation of $N_{Im}$-trityl-2-([1-fluoro-2-p-nitrophenylsulfinyl]ethyl)-$N_\alpha$-BOC-histidine methyl ester (2·X)

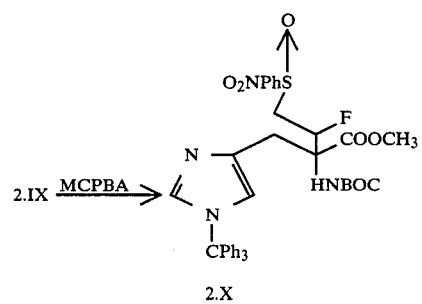

To 727 mg of compound 2·IX (1 mmole) in 25 ml of CH₂Cl₂ at 0° C. is added dropwise over 1 hour a solution of 172.6 mg (1 mmole); actually 203 mg of 85% pure) of MCPBA in 20 ml of CH₂Cl₂. The solution is aged 30 minutes at 25° C. and washed successively with aqueous NaHCO₃ and brine. Evaporation gives compound 2·X.

Step K: Preparation of 2-([1-fluoro-2-p-nitrophenylsulfinyl]ethyl)histidine hydrochloride (2·XI)

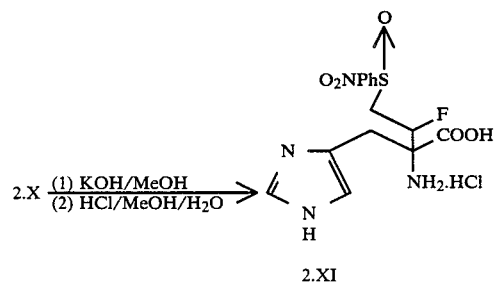

Compound 2·X, 745 mg, is treated with 60 mg of KOH (1.05 mmole) in 5 ml of MeOH for 2 hours at 45° C. to saponify the methyl ester. Then 25 ml 6N HCl in MeOH containing 5% by volume of water is added and the mixture is refluxed 3 hours to remove the trityl group. The reaction mixture is evaporated to dryness in vacuo, triturated with ether to remove trityl alcohol, and then taken up in 10 ml of ethanol. The KCl is filtered and the filtrate evaporated to afford compound 2·XI.

EXAMPLE 3

2-(p-nitrophenylsulfinyl)-3-chlorohistidine hydrochloride

Step A: Preparation of N$_{Im}$-trityl imidazole-4-carboxaldehyde (3·I)

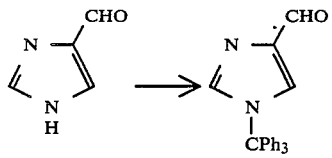

Imidazole 4-carboxaldehyde, 96 mg (1 mmole), is treated with 278.5 mg (1 mmole) of trityl chloride in 25 ml of DMF containing 139 µl of triethylamine (1 mmole) overnight. The DMF is pumped off in vacuo and the residue, taken up in benzene, is washed with dilute aqueous NaHCO$_3$ three times, then brine, then dried with K$_2$CO$_3$, filtered and evaporated to afford compound 3·I.

Step B: Preparation of N-BOC-S-p-nitrophenyl cysteine methyl ester (3·II)

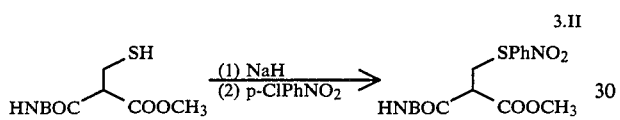

Cysteine N-BOC methyl ester, 235 mg (1 mmole), is treated with 24 mg of NaH (1 mmole) in dioxane with 20 mg of 15-crown-5, and then with 158 mg of p-chloronitrobenzene (1 mmole) at 100° C. for five hours. The dioxane is evaporated in vacuo, leaving crude 3·II.

Step C: Preparation of S-p-nitrophenyl cysteine methyl ester (3·III)

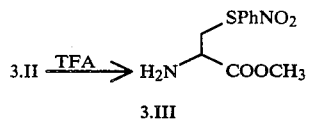

Crude II from Step B is taken up in 2 ml anisole and then treated at 0° C. for 11 minutes with 10 ml of TFA. The TFA and anisole are pumped off at 0.1 Torr at 30° C. and the residue partitioned between chloroform and aqueous 1N HCl. The aqueous layer is made to pH 9.0 with NaOH and extracted with CH$_2$Cl$_2$, providing a solution of compound 3·III.

Step D: Preparation of N-benzylidene S-p-nitrophenyl cysteine methyl ester (3·IV)

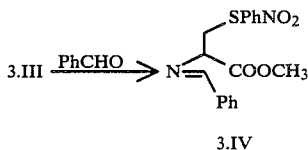

Compound 3·III, 256 mg (1 mmole), in 10 ml of CH$_2$Cl$_2$, is treated with 106 mg of benzaldehyde (1 mmole) for two hours at 25° C., then for a third hour with added MgSO$_4$ (100 mg). The solution is filtered and evaporated, affording compound 3·IV.

Step E: Preparation of N$_{Im}$-trityl N$_α$-benzylidene 2-(p-nitrophenylthio)-3-hydroxy histidine methyl ester (3·V)

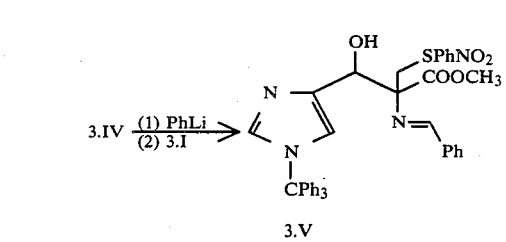

Compound 3·IV, 344 mg (1 mmole), is treated at −78° in 10 ml of THF with one equivalent of PhLi. After one minute, compound 3·I, 338 mg (1 mmole), is added, and the reaction allowed to warm to room temperature over 30 minutes. The solvent is evaporated and the residue is taken up in ether, washed with water and brine, dried with K$_2$CO$_3$, filtered and evaporated to afford compound 3·V.

Step F: Preparation of N$_{Im}$-trityl N$_α$-BOC 2-(p-nitrophenylthio)-3-hydroxy histidine methyl ester (3·VI)

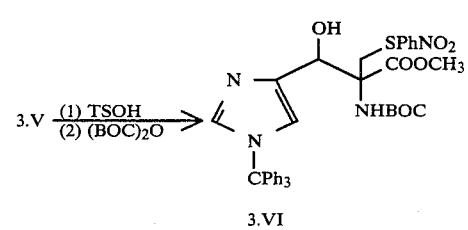

Compound 3·V, 682 mg (1 mmole), in 5 ml of anhydrous ether is added dropwise over 10 minutes to a solution of 190 mg of p-TSA·H$_2$O (1 mmole) in 20 ml of ether. The tosylate salt of the free N$_α$ amine is collected by decantation, stirred with CH$_2$Cl$_2$ and aqueous NaHCO$_3$. The organic layer is dried over K$_2$CO$_3$. The solution is filtered and treated with 218 mg of BOC$_2$O for three hours at 25° C. and then washed successively with water and brine, and dried with K$_2$CO$_3$. After filtration and evaporation, compound 3·VI is obtained.

Step G: Preparation of N$_{Im}$-trityl N$_{60}$-BOC 2-(p-nitrophenylthio)-3-chloro histidine methyl ester (3·VII)

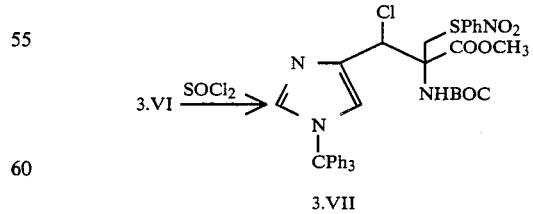

Compound 3·VI, 694 mg (1 mmole), is treated with 5 ml of pure SOCl$_2$ for one hour and then pumped in vacuo, affording compound 3·VII.

Step H: Preparation of N$_{Im}$-trityl N$_α$-BOC 2-(p-nitrophenylsulfinyl)-3-chloro histidine methyl ester (3·VIII)

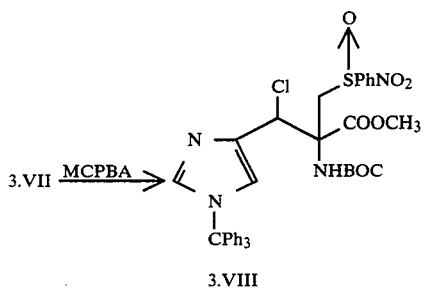

3.VII $\xrightarrow{\text{MCPBA}}$

3.VIII

To 713 mg of compound 3·VII (1 mmole) in 25 ml of CH$_2$Cl$_2$ at 0° C. is added dropwise over one hour a solution of 172.6 mg (1 mmole; actually 203 mg of 85% pure) of MCPBA in 20 ml of CH$_2$Cl$_2$. The solution is aged 30 minutes at 25° C. and washed successively with aqueous NaHCO$_3$ and brine to afford, after evaporation, compound 3·VIII.

Step I: Preparation of N$_{Im}$-trityl N$_\alpha$-BOC 2-(p-nitrophenylsulfinyl)-3-chloro histidine (3·IX)

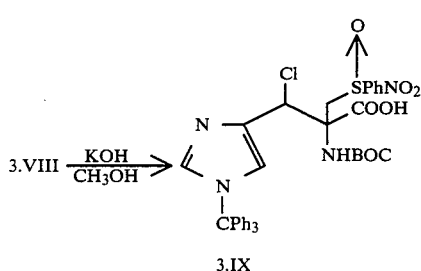

3.VIII $\xrightarrow{\text{KOH}}{\text{CH}_3\text{OH}}$

3.IX

Compound 3·VIII, 729 mg (1 mmole), is treated with 60 mg of KOH in 5 ml of MeOH for two hours at 45° C. to saponify the methyl ester, affording compound 3·IX in solution.

Step J: Preparation of 2-(p-nitrophenylsulfinyl)-3-chloro histidine hydrochloride (3·X)

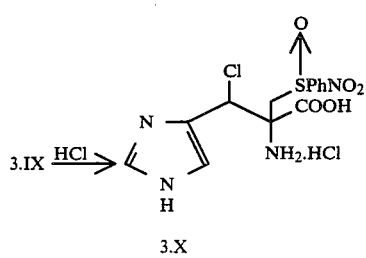

3.IX $\xrightarrow{\text{HCl}}$

3.X

To the solution of compound 3·IX from Step I is added 25 ml of 6N HCl in methanol+5% water. The mixture is refluxed three hours to remove the trityl and BOC groups. The product 3·X is isolated by evaporating the methanol, triturating with ether, taking it up in 10 ml of ethanol, filtration and evaporation.

The pharmaceutical formulations of this invention are illustrated in the following Examples which are meant to be illustrative only and not limiting with respect to type of formulation, nature of pharmaceutical carrier or proportions of ingredients.

EXAMPLE 4

| | TABLET Per tablet, mg. |
|---|---|
| Levodopa | 250 |
| 2-Fluoromethyl-3-(4-nitrophenylsulfinyl)-3-(3,4-dihydroxyphenyl)alanine | 25 |
| Lactose | 79.0 |
| Starch, corn | 65.0 |
| Hydroxypropyl cellulose (as 2% in ethanol) | 8.0 |
| Add: | |
| Starch, corn | 55.0 |
| Guar gum | 55.0 |
| Magnesium stearate | 4.0 |

The first four components are reduced to a fine powder by milling and remixing. The mixture is granulated with the hydroxypropyl cellulose solution. The wetted mass is passed through a No. 10 stainless steel screen and dried in the dark at 100° F. The dried granules are passed through a No. 20 stainless steel screen, and the additional quantity of corn starch, guar gum and magnesium stearate added. The mixture is compressed using a ½" standard curvature punch into tablets and the tablet may be coated with a conventional protective film containing various types of cellulose polymers, dyes and opacifying agents.

EXAMPLE 10

Injectable Preparation 2-(p-Nitrophenylsulfinyl)-3-chlorohistidine hydrochloride 25 mg.
Pyrogen fee water to 1 ml.
Sterilize by filtration and seal under nitrogen.
What is claimed is:
1. A compound of the structural formula:

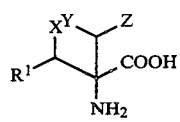

or a pharmaceutically acceptable salt thereof wherein X is hydrogen, fluoro, chloro, bromo, iodo, C$_{2-4}$ alkanoyloxy, toluenesulfonyloxy, benzenesulfonyloxy, C$_{1-3}$ alkanesulfonyloxy, p-nitrobenzoyloxy, or

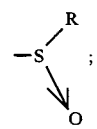

Y is hydrogen or

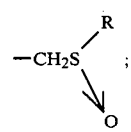

and Z is fluoro, chloro, bromo, iodo, C$_{2-4}$ alkanoyloxy, toluenesulfonyloxy, benzenesulfonyloxy, C$_{1-3}$ alkanesulfonyloxy, p-nitrobenzoyloxy, or

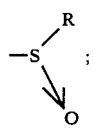

or Y and Z taken together form $=CH_2$; with the proviso that one and only one of X, Y and Z is a sulfoxide, and one and only one of X and Z is halo;
wherein
R is
(1) phenyl,
(2) nitrophenyl,
(3) cyanophenyl,
(4) $C_{1-3}$ alkylsulfonylphenyl,
(5) $C_{1-3}$ alkoxycarbonylphenyl,
(6) di(trifluoromethyl)phenyl,
(7) o-$C_{1-3}$ alkylphenyl, or
(8) o,o-di($C_{1-3}$ alkyl)phenyl, and
$R^1$ is
aminoethyl, or
hydrogen.

2. The compound of claim 1 which is
2,5-diamino-2-fluoromethyl-3-(p-nitrophenylsulfinyl)pentanoic acid; or
2,5-diamino-2-([1-fluoro-2-p-nitrophenylsulfinyl]ethyl)pentanoic acid;
or a pharmaceutically acceptable salt thereof.

3. A pharmaceutical enzyme inhibiting composition comprising a pharmaceutical carrier and an effective enzyme inhibiting amount of a compound of structural formula:

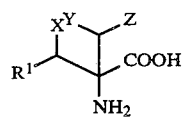

or a pharmaceutically acceptable salt thereof wherein X is hydrogen, fluoro, chloro, bromo, iodo, $C_{2-4}$ alkanoyloxy, toluenesulfonyloxy, benzenesulfonyloxy, $C_{1-3}$ alkanesulfonyloxy, p-nitrobenzoyloxy, or

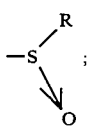

Y is hydrogen or

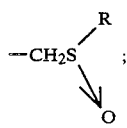

and Z is fluoro, chloro, bromo, iodo, $C_{2-4}$ alkanoyloxy, toluenesulfonyloxy, benzenesulfonyloxy, $C_{1-3}$ alkanesulfonyloxy, p-nitrobenzoyloxy, or

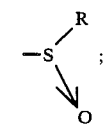

or Y and Z taken together form $=CH_2$; with the proviso that one and only one of X, Y and Z is a sulfoxide, and one and only one of X and Z is halo;
wherein
R is
(1) phenyl,
(2) nitrophenyl,
(3) cyanophenyl,
(4) $C_{1-3}$ alkylsulfonylphenyl,
(5) $C_{1-3}$ alkoxycarbonylphenyl,
(6) di(trifluoromethyl)phenyl,
(7) o-$C_{1-3}$ alkylphenyl, or
(8) o,o-di($C_{1-3}$ alkyl)phenyl, and
$R^1$ is
aminoethyl, or
hydrogen.

4. The pharmaceutical composition of claim 3 wherein the compound is
2,5-diamino-2-fluoromethyl-3-(p-nitrophenylsulfinyl)pentanoic acid; or
2,5-diamino-2-([1-fluoro-2-p-nitrophenylsulfinyl]ethyl)pentanoic acid;
or a pharmaceutically acceptable salt thereof.

5. A method of inhibiting enzymes in a patient in need of such treatment which comprises the administration of an enzyme inhibitory amount of a compound of structural formula:

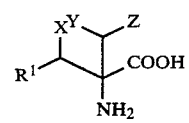

or a pharmaceutically acceptable salt thereof wherein X is hydrogen, fluoro, chloro, bromo, iodo, $C_{2-4}$ alkanoyloxy, toluenesulfonyloxy, benzenesulfonyloxy, $C_{1-3}$ alkanesulfonyloxy, p-nitrobenzoyloxy, or

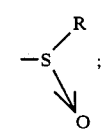

is hydrogen or

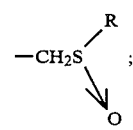

and Z is fluoro, chloro, bromo, iodo, $C_{2-4}$ alkanoyloxy, toluenesulfonyloxy, benzenesulfonyloxy, $C_{1-3}$ alkanesulfonyloxy, p-nitrobenzoyloxy, or

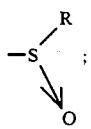

or Y and Z taken together form =CH$_2$; with the proviso that one and only one of X, Y and Z is a sulfoxide, and one and only one of X and Z is halo;
wherein
R is
  (1) phenyl,
  (2) nitrophenyl,
  (3) cyanophenyl,
  (4) C$_{1-3}$ alkylsulfonylphenyl,
  (5) C$_{1-3}$ alkoxycarbonylphenyl,
  (6) di(trifluoromethyl)phenyl,
  (7) o-C$_{1-3}$ alkylphenyl, or
  (8) o,o-di(C$_{1-3}$ alkyl)phenyl, and
R$^1$ is
  aminoethyl, or
  hydrogen.

6. The method of claim 5 wherein the compound is
2,5-diamino-2-fluoromethyl-3-(p-nitrophenylsulfinyl)pentanoic acid; or
2,5-diamino-2-([1-fluoro-2-p-nitrophenylsulfinyl]ethyl)pentanoic acid;
or a pharmaceutically acceptable salt thereof.

* * * * *